(12) United States Patent
Zainiev et al.

(10) Patent No.: US 8,153,403 B1
(45) Date of Patent: Apr. 10, 2012

(54) PROCESS FOR IDENTIFYING EXISTENCE OF SINGLE NUCLEOTIDE POLYMORPHISM WITHOUT DNA SEQUENCING

(76) Inventors: Gafur Zainiev, West Bloomfield, MI (US); Inlik Zainiev, West Bloomfield, MI (US); Timur Zainiev, West Bloomfield, MI (US)

( * ) Notice: Subject to any disclaimer, the term of this patent is extended or adjusted under 35 U.S.C. 154(b) by 0 days.

(21) Appl. No.: 12/714,974

(22) Filed: Mar. 1, 2010

Related U.S. Application Data

(63) Continuation-in-part of application No. 12/049,679, filed on Mar. 17, 2008, now abandoned.

(60) Provisional application No. 60/895,193, filed on Mar. 16, 2007.

(51) Int. Cl.
*C12P 19/34* (2006.01)
*C12Q 1/68* (2006.01)

(52) U.S. Cl. ........................................ 435/91.2; 435/6.1

(58) Field of Classification Search ............. 435/6, 91.2, 435/6.1
See application file for complete search history.

(56) References Cited

U.S. PATENT DOCUMENTS
6,821,734 B2 * 11/2004 Kambara et al. ................ 435/6
* cited by examiner

*Primary Examiner* — Gary Benzion
*Assistant Examiner* — Cynthia Wilder
(74) *Attorney, Agent, or Firm* — Patent Procurement Services

(57) ABSTRACT

A process for detecting the presence of a mutation in an oligonucleotide strand such as a DNA strand from a gene without the need for DNA sequencing is provided. The inventive process provides a rapid pre-test to screen for the presence or absence of a mutation in a target gene of a subject to determine whether laborious sequencing protocols are required to further characterize a mutation. The inventive process provides a rapid screening protocol for identifying and detecting a genetic mutation in a patient who presents with a disease.

10 Claims, 1 Drawing Sheet

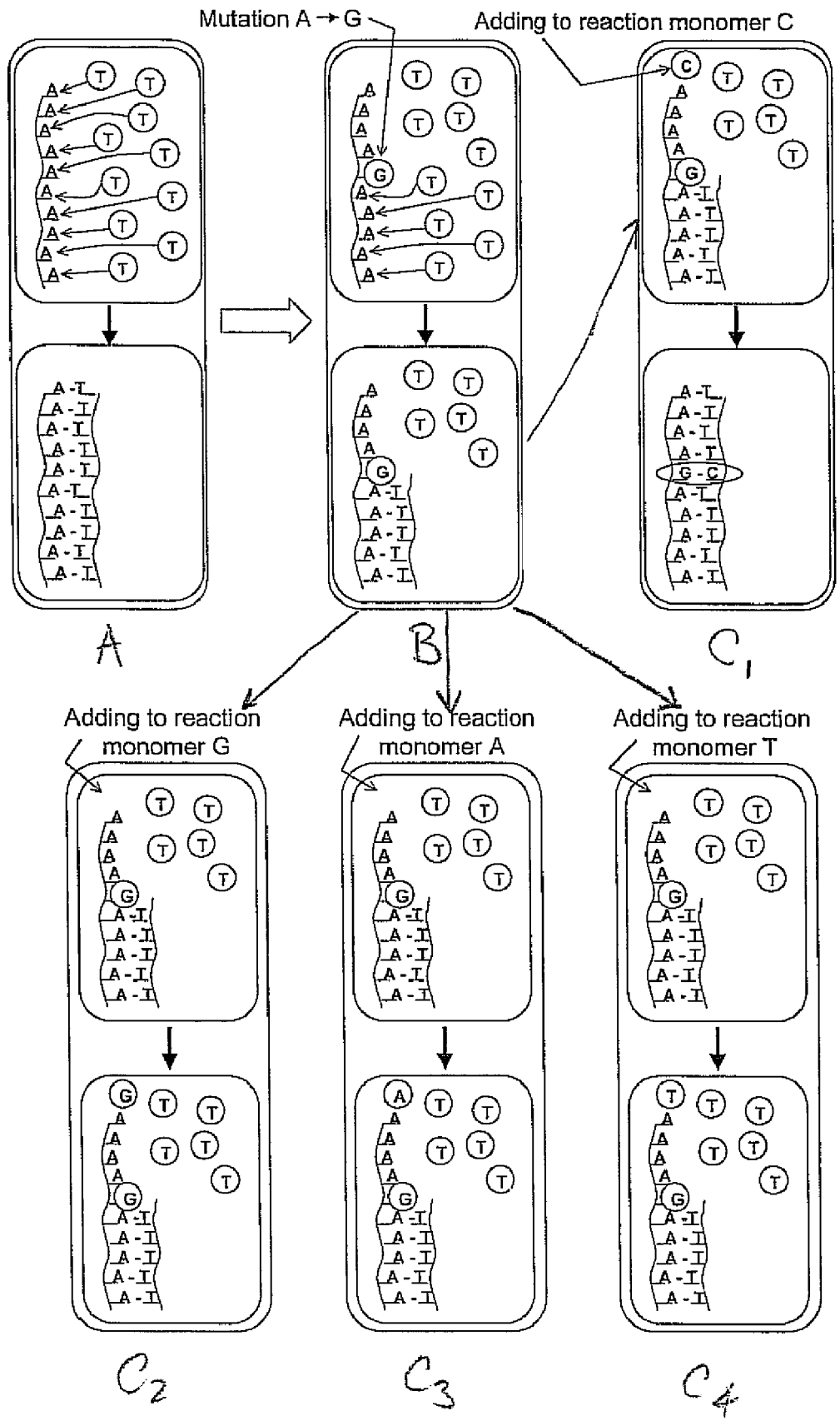

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: template strand

<400> SEQUENCE: 1
atgcatgcat gcatgcatgc atgcatgcat                                  30

<210> SEQ ID NO 2
<211> LENGTH: 30
<212> TYPE: DNA
<213> ORGANISM: Artificial Sequence
<220> FEATURE:
<223> OTHER INFORMATION: forward primer

<400> SEQUENCE: 2
tacgtacgta cgtacgtacg tacgtacgta                                  30
```

PROCESS FOR IDENTIFYING EXISTENCE OF SINGLE NUCLEOTIDE POLYMORPHISM WITHOUT DNA SEQUENCING

CROSS REFERENCE TO RELATED APPLICATIONS

This invention is a continuation-in-part of U.S. utility application Ser. No. 12/049,679 filed 17 Mar. 2008 which in turn claims priority from U.S. Provisional Application 60/895,193 filed Mar. 16, 2007 the entire disclosure of these applications are hereby incorporated by reference.

FIELD OF THE INVENTION

The present invention relates in general to DNA strand synthesis and in particular to a process of identifying the existence of single nucleotide polymorphisms (SNPs) without resort to DNA sequencing.

BACKGROUND OF THE INVENTION

An ability to test for mutations in a DNA molecule is an important part of modern medical diagnostics. Current testing methods identify gene and other DNA mutations by reading the sequence of a long length of or the entire sequence of a DNA molecule under investigation and then comparing the identified sequence to the known mutation-free sequence for the DNA or gene of interest.

The art of DNA sequencing, long accomplished by a multi-step brute force approach, was radically transformed by the development of new technologies during the human genome project advancing the pace of sequencing a genome from years to months. Completion of the human genome project saw successful innovations in the fields of recombinant protein engineering, fluorescent dyes, capillary electrophoresis, automation, informatics and process management. (Metzger, M. L., *Genome Res*, 2005; 15:1767-76).

Modern sequence analysis is most commonly directed toward discovery and analysis of sequence variation as it relates to human health and disease. These continue to be large-scale projects that are plagued by technology that is slow in its application and inaccurate in its nature. Further, current technologies available for sequence analysis tend to require large amounts of nucleic acid template and large biological samples. Important parameters which can be addressed by improved technology include increased sequencing speed, increases in sequence read length achievable during a single sequencing run, decreasing in the amount of template required to obtain positive sequence results, decreasing the amount of reagent required for processing a sequence reaction, improving the accuracy and reliability of the sequences generated, and improved identification of nucleic acid repeats in the strand of DNA.

Several unique approaches are traditionally employed for sequencing DNA. The most common is the dideoxy-termination method of Sanger (Sanger et al., *PNAS USA*, 1977; 74:563-567). Single nucleotide analysis such as pyro-sequencing first described by Hyman 1988 (*Analytical Biochemistry*, 174, pages 423-436) has proved to be the most successful non-Sanger method. Cyclic reversible termination or CRT has also been employed with some success. Finally, sequence analysis has been accomplished by an exonuclease reaction wherein particular nucleotide residues are identified in a step-wise fashion as they are removed from the end of an oligonucleotide strand.

The Sanger method represents a mixed mode process coupling synthesis of a complementary DNA template using deoxynucleotides (dNTPs) with synthesis termination by the use of fluorescently labeled dideoxynucleotides (ddNTPs). Balancing reagents between natural dNTPs and ddNTPs leads to the generation of a set of fragments terminating at each nucleotide residue within the sequence. The individual fragments are then detected following capillary electrophoresis so as to resolve the different oligonucleotide strands. The sequence is determined by identification of the fluorescent profile of each length of fragment. This method has proven to be both labor and time intensive and requires extensive pretreatment of the DNA source. Microfluidic devices for the separation of resulting fragments from Sanger sequencing has improved sample injection and even decreased separation times, hence, reducing the overall time and cost of a DNA sequencing reaction. However, the time and labor required to successfully prosecute a Sanger method is still sufficiently great to make several studies beyond the reach of many research labs.

The single nucleotide addition methodology of pyro-sequencing has been the most successful non-Sanger method developed to date. Pyro-sequencing capitalizes on a non-fluorescence technique, which measures the release of inorganic phosphate converted to visible light through a series of enzymatic reactions. This method does not depend on multiple termination events, such as in Sanger sequencing, but instead, relies on low concentration of substrate dNTPs, so as to regulate the rate of dNTP synthesis by DNA polymerase. As such, the DNA polymerase extends from the primer, but pauses when a non-complementary base is encountered until such time as a complementary dNTP is added to the sequencing reaction. This method, over time, creates a pyrogram from light generated by the enzymatic cascade, which is recorded as a series of peaks and corresponds to the order of complementary dNTPs incorporated revealing the sequence of the DNA target. (See Ronaghi, *Science*, 1998; 281:363-65; Ronaghi, *Analytical Biochemistry*, 2002; 286:282-288; Langaeet and Ronaghi, *Mutational Research*, 2005; 573:96-102). While pyro-sequencing has the potential of reducing sequencing time, as well as amount of template required, it is typically limited to identifying 100 bases or less. Further, repeats of greater than five nucleotides are difficult to quantitate using pyro-sequencing methods. Also, pyro-sequencing methods must be carefully designed, as it is the order of dNTP addition that determines the pyrogram profile and investigators must design experiments so as to avoid asynchronistic extensions of heterozygous sequences as almost half of all heterozygous sequences result in asynchronistic extensions at the variable site. (Metzger, 2005).

Cyclic Reversible Termination (CRT) uses reversible terminating deoxynucleotides, which contain a protecting group that serves to terminate DNA synthesis. A termination nucleotide is incorporated, imaged, and then deprotected so that the polymerase reaction may incorporate the next nucleotide in the sequence. CRT has advantages over pyro-sequencing in that all four bases are present during the incorporation phase, not just a single base during a single period of time. Single base addition is achievable through homopolymer repeats and synchronistic extensions are easily maintained past heterozygous bases. Perhaps the greatest advantage of CRT is that it may be performed on many highly parallel platforms, such as high-density oglionucleotide arrays (Pease et al., 1994, and Albert et al., 2003), PTP arrays (Layman et al., 2003), or random dispersion of single molecules (Nutra and Church, 1999). High-density arrays and incorporation of di-labeled dideoxynucleotide dNTPs by DNA polymerase gives CRT significant improvement in throughput and accuracy. However, CRT suffers several drawbacks including short read lengths that must be overcome before it can be widely employed.

Finally, exonuclease methods sequentially release fluorescently labeled bases as a second step following DNA polymerization to a fully labeled DNA molecule. Using a hydrodynamic flow detector, each dNTP analog is detected by its fluorescent wavelength as it is cleaved by the exonuclease. This method has several drawbacks. For example, the DNA polymerase and, more importantly, the exonuclease must have high activity on the modified DNA strand and generation of a DNA strand fully incorporating four different fluorescent dNTP analogs has yet to be achieved.

Technological advances in fluorescence detection are essential to decrease the amount of target oglionucleotide necessary for sequencing analysis. Four color fluorescent systems such as those employed in Sanger methods have several disadvantages including inefficient excitation of fluorescent dyes, significant spectra overlap between each of the dyes, and inefficient collection of the emission signal. Several dyes have been recently developed that help address these issues, such as fluorescence resonance energy transfer (FRET) dyes (Ju et al., *PNAS*, 1995; 92:4347-51; Metzger, *Science*, 1996: 271:1420-1422.) Additional strategies have been proposed, such as fluorescence lifetime and a radio frequency modulation. Finally, Lewis et al. recently described termed pulse multiline excitation (PME) which is an ineffective method for multifluorescence discrimination. (Lewis, *PNAS*, 2005: 102:5346-41).

The demand for rapid small and large scale DNA sequencing has radically increased over the last several years. Current sequencing methods described supra or otherwise known in the art are expensive and time consuming. Further, the prior art methods each suffer the drawback of inaccuracy in identification of repeat nucleotides in the sequence.

As the majority of DNA sequence mutations are present in a minority of subjects, DNA screening most often does not identify a mutation, Therefore, it is advantageous to "pre-test" DNA molecules to first determine whether one or more DNA mutations exist before isolating the particular location in the sequence that harbors the mutation. A "pre-test" is quicker and less expensive than the full-blown mutation or mutational screening test, thus, DNA mutation testing will become a much more affordable and popular in practice.

Thus, there exists a need for a quick and inexpensive genetic mutation pre-test, which determines whether a DNA molecule in question has a mutation without requiring reading the DNA sequence and without a need to identify the location of the actual mutation.

SUMMARY OF THE INVENTION

A process of identifying the existence of a mutation in a DNA strand without DNA sequencing is provided wherein a plurality of DNA single strands of a DNA sequence in a solution is combined with a stoichiometric quantity of monomeric nucleotide bases to synthesize complementary second strands to the plurality of DNA single strands in the presence of species and conditions for DNA synthesis to which a small excess of monomeric nucleotide bases beyond the stoichiometric quantity of monomeric nucleotide bases needed to synthesize complementary second strands is added to the solution and a sufficient time for DNA synthesis is allowed. Detection of whether a quantity of monomeric nucleotide bases remaining in the solution after DNA synthesis is more than the small excess of monomeric nucleotide bases as being indicative of a mutation being present in said plurality of DNA single strands.

The process uses a plurality of DNA single strands of a DNA sequence that is a known DNA sequence, a known DNA sequence with a mutation, or where the mutation is one or more small nucleotide polymorphisms. The process uses a plurality of DNA single strands in excess of 500 copies and a small excess between 0.3 and 3 number percent or preferably between 0.5 and 1.5 number percent.

The process also is performed by adding a single type monomer possibly depleted in the solution after DNA synthesis under conditions for DNA synthesis; and detecting the presence or absence of synthesis of the complementary second strand.

The process further repeats the adding and detecting steps with other single monomer species other than the single type monomer species in the solution or an aliquot of the solution. The four separate monomers of A, T, C and G are added to aliquots of the solution.

Finally, the process also provides sequencing the DNA single strand before or after synthesis of said complementary second strands.

BRIEF DESCRIPTION OF THE DRAWINGS

FIG. 1, FIGS. 1A-1C4 are schematics depicting DNA second strand from (FIG. 1A) a SNP-free first DNA strand consuming all the nucleotide monomer; (FIG. 1B) a first DNA strand having a SNP resulting in unused nucleotide monomer; (FIG. 1C1) with the addition of the complementary monomer nucleotide (C) of the SNP to the FIG. 1B system to complete second strand synthesis; (FIG. 1C2) with the addition of a non-complementary monomer nucleotide (G) of the SNP to the FIG. 1B system precluding second strand synthesis; (FIG. 1C3) with the addition of a non-complementary monomer nucleotide (A) of the SNP to the FIG. 1B system precluding second strand synthesis; and (FIG. 1C4) with the addition of a non-complementary monomer nucleotide (T) of the SNP to the FIG. 1B system precluding second strand synthesis.

DETAILED DESCRIPTION OF THE PREFERRED EMBODIMENTS

The present invention is directed to a rapid process to identify the presence of a mutation in a gene or oligonucleotide strand. Without limitation the present invention is directed to a process of identifying a small nucleotide polymorphism in a subject without the need for sequencing an entire target gene or undergoing rigorous analysis to locate a mutation that may or may not be present. Thus, the subject invention has utility as a rapid method to pre-test a DNA sequence for the presence of a mutation.

As used herein the term DNA illustratively refers to an oligionucleotide. An oligonucleotide is comprised of a plurality of nucleotides that are illustratively, nucleotides, ribonucleotides, deoxynucleotides, dideoxynucleotides, peptide nucleotides, modified nucleotides, modified peptide nucleotides, modified phosphate sugar backbone nucleotides, amino acids, or modified amino acids. DNA is optionally single stranded, double stranded, triple stranded, or other multimers of strands associated in relation to the sequence of nucleotides.

As used herein nucleotides are preferably deoxynucleotides. Preferably, deoxynucleotides are adenine (A), guanine (G), thymine (T), cytosine (C), uracil (U), synthetic nucleotides, modifications thereof, or combinations thereof. Other types and forms of nucleotides are known in the art and are appreciated to be similarly operable herein. It is appreciated that a single nucleotide is optionally referred to herein as a monomer or a monomeric nucleotide base.

As used herein, a "stoichiometric quantity of monomeric nucleotide base" is defined as the number of molecules of monomeric nucleotide base needed to synthesize complementary second strands for all the target DNA strands present in a solution.

As used herein, a subject illustratively includes: humans; non-human primates illustratively including monkey, chimpanzee, and others; horses; goats; cows; sheep; pigs; dogs; cats; guinea pigs; hamsters; rabbits; mice; rats; and other rodents; cells, tissues, synthetic organic or inorganic molecules, or combinations thereof A subject is illustratively a patient.

As used herein, the term biological sample illustratively includes whole blood, plasma, serum, extracellular fluid, cytosolic fluid, tissue, solubilized cellular membrane samples, cultured cells, cell culture media, physiological buffers, combinations thereof, or other biologicals known in the art.

As used herein, the term gene illustratively includes any oligonucleotide sequence, transfection or translation products thereof, regulatory sequences illustratively including but not limited to promoters, enhancers, DNA recognition elements, 3' or 5' untranslated regions, exons, introns, or any translated or untranslated region of the DNA of a subject.

The inventive process capitalizes on a known wild-type sequence of DNA. The human genome project combined with countless other sequencing studies has made available the wild-type of sequence of most every gene in a wide variety of subjects. The instant inventive process capitalizes on this information to determine a stoichiometric amount of nucleotides to use for second strand DNA synthesis and identification of a mutation in one or more genes of a subject.

Since the unmutated wild-type sequence of the tested DNA molecule is known in advance, it is possible to fully synthesize the complementary second strand by adding to solution a single DNA strand, all types of required molecules (replication machinery, cofactors, ions, etc. such as a polymerase, etc.) and a correct stoichiometric number monomers.

In a non-limiting example, an exemplary DNA sequence contains 100 A monomers and 60 G monomers, then putting into solution a single strand of such molecule along with 100 T and 60 C monomers will result in full synthesis, which can be confirmed by observing no free monomers left in the solution. Illustratively, in the presence of a mutation such as a SNP, instead of 100 A and 60 G monomers, an illustrative DNA strand contains 99 A and 61 G monomers. After adding 100 T and 60 C monomers and all necessary replication machinery and suitable replication conditions for complementary strand synthesis there would be at least one T monomer left in a solution. Observation of this monomer signals the presence of a mutation and indicates that a more expensive and thorough test is appropriate to identify the site of the mutation.

DNA is illustratively comprised of four monomer species. Thus, adding to a solution the exact number of complementary monomers to a single strand DNA molecule would also leave at least one monomer not included in the second strand if there was a mutation and one nucleotide monomer base in a sequence was replaced by another base.

To ensure reliable synthesis the number of complementary monomers preferably exceeds the number of monomers in the sequence. However, the number of excess monomers necessary for reliable synthesis does not scale with the number of copies of DNA strands synthesized in the solution. Illustratively, if it takes extra 10 monomers to reliably synthesize the second strand, it would not take extra 1,000 extra monomers to synthesize 100 identical second strands in a single solution. Instead, it would take the same extra 10 monomers. This is exemplary of the small excess of monomeric nucleotides beyond the stoichiometric quantity of nucleotides detailed with respect to the present invention.

Illustratively, as shown in FIGS. 1A and 1B, to test for the existence of one or more mutations in a given DNA molecule, 1,000 single-strand DNA copies are placed in a solution and the corresponding number of complementary monomers added. After stoichiometric monomeric base addition, a small excess 0.3-3 number % excess and preferably 1% excess copies of each monomer are added. It is appreciated that the number percent is any number between 0.01% and 10%. It is further appreciated that any operable number percent is operable herein. Following synthesis, if there is an A to G mutation in a target sequence and, for example, 10 excess of each monomer type is present, then after the synthesis is complete at least 990 free T monomers will remain in the solution and unincorporated into the complementary second DNA strand. Alternatively, if the target DNA strand is identical to the known wild-type sequence, then after synthesis 10 free monomers will remain in the solution. Since it is very easy to visually distinguish 10 free monomers from 990 free monomers in a solution, the test will produce a reliable prediction whether or not the target DNA molecule has a mutation relative to wild-type.

After completing synthesis of a complementary second DNA strand the amount of monomers remaining in solution is measured by any appropriate means known in the art. Should the number of monomers in solution indicate the presence of a mutated or other non-wild-type sequence, an amount of one known type of monomer proportional to the number of DNA strands originally placed in solution is be added into the reactor. Should the added monomer be complementary to the mutated base present in the target strand, it will be incorporated into the complementary second strand and the number of free monomers in solution is decreased to the level observed after the synthesis of a wild-type DNA template. When the added monomer is non-complementary to the mutated base present in the target strand, the amount of free monomers in solution increases.

In a preferred embodiment, as depicted in FIGS. 1C1-1C4, greater reliability is achieved when multiple reaction chambers are used in parallel. Preferably, the number of reactors is proportional to the number of monomer species present in the target DNA strand. In a most preferred embodiment, four reactors are operated in parallel that each house a solution containing an identical number of target DNA strands. Should the initial synthesis of a complementary second strand indicate the presence of a mutation by an excess of monomers present in the solution, a single unique monomer species is added to each of the four reaction chambers. In three of the reaction chambers the number of free monomers will not decrease significantly. However, in the chamber wherein the single unique monomer species is complementary to the mutated nucleotide in the target sequence, the number of free monomers will decrease to the level present should the target strand be wild-type, Thereby, identification of the nucleotide of the mutation is identified.

In a most preferred embodiment, the inventive process provides N identical single-strand copies of DNA placed into solution in a reaction chamber, wherein each strand contains $M_A$ copies of monomer A, $M_T$ copies of monomer T, $M_G$ copies of monomer G, and $M_C$ copies of monomer C. To solution is then added $M_A*N$ copies of free monomer T, $M_T*N$ copies of free monomer A, $M_G*N$ copies of free monomer C, and $M_C*N$ copies of free monomer G are placed in the same solution. Additionally, m copies each of monomers A, T, G, and C are placed in the solution. After synthesis of the second DNA strand takes place, the solution contains one of the following:

1. N copies of a double-stranded DNA molecule and 4*m free monomers representing a wild-type sequence; or
2. N incomplete copies of a double-stranded DNA molecule and at least N+4*m free monomers representing a mutant sequence.

The type or species of the monomers that remain in the solution after complementary second strand synthesis is irrelevant.

If N+4*m>>4*m then it will be possible to experimentally distinguish situations 1 and 2. If situation 1 is observed (i.e. a very small fixed number of free monomers), then there are no single nucleotide mutations in a DNA molecule. If situation 2 is observed (a large number of free monomers), then there is at least one mutation in a DNA molecule.

It is appreciated that the oligonucleotide, or target DNA template strand, is immobilized on a support, or free in solution.

The polymerization enzyme responsible for the polymerization reaction synthesizing the complementary second strand or all other polymerization reactions is optionally a thermostable polymerase or a thermodegradable polymerase, a DNA polymerase, an RNA polymerase, a reverse transcriptase, combinations thereof, or mixtures thereof.

As opposed to the template being attached to a support, the polymerization enzyme is optionally attached to the support, or is itself free in solution. Template strand types operable in the herein illustratively include double-stranded DNA, single-stranded DNA, single-stranded DNA hairpins, RNA, and RNA hairpins. The template is optionally attached to a support by hybridizing to a primer sequence that is itself optionally affixed to a support. Alternatively, the primer sequence is free in solution and is complementary to a small segment of the target sequence so that a polymerization reaction may be extended from the primer.

Monomers optionally comprise a label or a plurality of labels. Numerous label types are operable in the instant invention illustratively including chromophores, fluorescent moieties, haptens, enzymes, antigens, dyes, phosphorescent groups, chemiluminescent moieties, scattering or fluorescent nanoparticles, FRET donor or receptor molecules, Raman signal generating moieties, precursors thereof, cleavage products thereof, and combinations thereof. In addition, photobleachable, photoquenchable, or otherwise inactivatable labels are similarly operable. The label is optionally attached to a monomer at any suitable site illustratively including a base, a sugar moiety, an alpha phosphate, beta phosphate, gamma phosphate, or combinations thereof. It is appreciated that each homogeneous species of monomer optionally carries a label that is distinguishable from other labels on different monomer species.

Detection of free monomer(s) is accomplished by one or many of numerous identifying techniques; illustratively, far field microscopy, near field microscopy, evanescent wave or wave guided illumination, nanostructure enhancement, photon excitation, multiphoton excitation, FRET, photo conversion, spectral wavelength discrimination, fluorophore identification, background suppression, mass spectroscopy, chromatography, electrophoresis, surface plasmon resonance, enzyme reaction, fluorescence lifetime measurements, radio frequency modulation, pulsed multiline excitation, combinations thereof, or other techniques known in the art.

Background fluorescence or fluorescence of previously added monomers to a growing structure is optionally eliminated by photobleaching the label, cleaving the label, or otherwise inactivating the label. The label is optionally cleaved from the backbone prior or subsequent to addition of additional monomers.

The present invention also envisions use of an apparatus such as that described in U.S. patent application Ser. No. 11/835,054 the entire disclosure of which is hereby incorporated by reference.

In a non-limiting example, an unidentified DNA template sequence is resolved by the instant inventive process. DNA is illustratively comprised of four element types, an A, T, and C. It is appreciated that DNA is optionally synthesized in vitro in a chamber in the presence of all required molecules illustratively including a DNA polymerase and a helicase. It is further appreciated that with a given sequence of DNA only one of the four types of elements A, T, G or C will be assembled at each hybridization site onto the target DNA strand. It is known in the art that A hybridizes to T, and G hybridizes to C. According to the inventive process DNA synthesis is illustratively performed using four chambers with the appropriate number of DNA molecule copies in each chamber.

The inventive process is operable for many different types of sequence structures or monomer containing structures. A monomer is illustratively a nucleotide, a ribonucleotide, deoxyribonucleotide, deoxynucleotide, peptide nucleotide, modified nucleotide, modified peptide nucleotide, modified phosphate sugar backbone nucleotide, amino acid, or modified amino acids.

Illustratively, a DNA template is a DNA oligonucleotide sequence. Template DNA is optionally free in solution or bound to a support in a reaction chamber or to the reaction chamber wall itself. Immobilization of the template is accomplished through conventional techniques known in the art illustratively including covalent attachment to a functional group on the solid surface, or by biotin/avidin interaction. In an optional embodiment a short oligonucleotide primer is bound to a support. The oligonucleotide segment is complementary to a small known sequence on the DNA template strand. Hybridization of the DNA template strand with the surface bound oligonucleotide immobilizes the DNA template to the surface of the chamber in reversible fashion. This embodiment has the additional advantage of providing a primer sequence for a polymerization reaction to occur. It is common in the art of DNA sequencing analyses that small segments of known sequence are present at the termination of each unknown strand. The template strand is optionally double stranded DNA, single stranded DNA, single stranded DNA hairpins, RNA, or RNA hairpins.

The inventive process further comprises a polymerization reaction in which a monomer or plurality of monomers are added to a growing complementary second strand DNA structure in a complementary fashion. The polymerization reaction is illustratively performed by a nucleic acid polymerizing enzyme that is illustratively a DNA polymerase, RNA polymerase, reverse transcriptase, or mixtures thereof. It is further appreciated that accessory proteins or molecules are present to form the replication machinery. In a preferred embodiment the polymerizing enzyme is a thermostable polymerase or thermodegradable polymerase. Use of thermostable polymerases is well known in the art such as Taq polymerase available from Invitrogen Corporation. Thermostable polymerases allow synthesis reaction to be initiated or shut down by a change in temperature or other condition in the chamber without destroying activity of the polymerase.

Accuracy of the base pairing in the preferred embodiment of DNA sequencing is provided by the specificity of the enzyme. Error rates for Taq polymerase tend to be false base incorporation of $10^{-5}$ or less. Johnson, *Annual Reviews of Biochemistry*, 1993: 62:685-713; Kunkel, *Journal of Biological Chemistry*, 1992; 267:18251-18254 (both of which are hereby incorporated by reference.) Specific examples of thermostable polymerases illustratively include those isolated from *Thermos aquaticus, Thermos thermophilus, Pyrococcus woesei, Pyrococcus furiosus, Thermococcus litoralis* and *Thermotoga maritima*. Thermodegradable polymerases illustratively include *E. coli* DNA polymerase, the Klenow fragment of *E. coli* DNA polymerase, T4 DNA polymerase, T7 DNA polymerase and other examples known in the art. It is recognized in the art that other polymerizing enzymes are similarly suitable illustratively including *E. coli*, T7, T3, SP6 RNA polymerases and AMV, M-MLV, and HIV reverse transcriptases.

The polymerases are optionally bound to a primer template sequence. When the template sequence is a single-stranded DNA molecule the polymerase is bound at the primed end of the single-stranded nucleic acid at an origin of replication or with double stranded DNA to a nick or gap. Similarly, secondary structures such as in a DNA hairpin or an RNA hairpin allow priming to occur and replication to begin. A binding site for a suitable polymerase is optionally created by an accessory protein or by any primed single-stranded nucleic acid.

In a preferred embodiment the DNA template strand is bound to a support located within the chamber. Materials suitable for forming a support optionally include glass, glass with surface modifications, silicon, metals, semiconductors, high refractive index dielectrics, crystals, gels and polymers. A support is illustratively a planar or spherical surface. It is appreciated in the inventive process that either a sequencing primer, a target nucleic acid molecule, or the nucleic acid polymerizing enzyme are illustratively immobilized on the support. A complementary bonding partner for forming interactions with any of the above molecules or any other of the operational machinery in the inventive process are similarly appreciated to be suitable for immobilizing material onto a surface. Interaction of any of the replication machinery with the surface is optionally nonspecific. Examples of a specific type bonding interaction include a biotin/streptavidin linkage wherein a known primer sequence is optionally labeled with a biotin molecule and the solid support is labeled with a streptavidin molecule. When the biotinylated primer is added to the chamber a tight bonding interaction between the biotin and streptavidin occurs immobilizing the primer sequence onto the support surface. It is further appreciated that the target DNA sequence is optionally labeled itself so that it is immobilized on the support surface. Additionally, a primer sequence is optionally immobilized by hybridization with a complementary immobilized oligonucleotide. Thus, a primary oligonucleotide is immobilized on a surface with a short sequence complementary to the primer oligonucleotide. It is preferred that the primer oligonucleotide is of sufficient additional length that hybridization between the immobilized nucleotide and the primer oligonucleotide allows base pairing between the primer oligonucleotide and the target DNA sequence, thus, binding the target DNA sequence to the support surface. Interaction of any suitable molecule to the support surface is appreciated to be reversible or irreversible. Alternative exemplary methods for immobilizing sequencing primer or target nucleic acid molecule to a support include antibody antigen binding pairs or photoactivated coupling molecules. It is appreciated in the art that numerous other immobilizing methods are similarly suitable in the inventive process.

It is further appreciated that the protein material of the polymerization enzyme or replication machinery is optionally immobilized on the surface either reversibly or irreversibly. For example, RNA polymerase was successfully immobilized on activated surface without loss of catalytic activity. Yin et al., *Science*, 1995; 270: 1653-57, which is hereby incorporated by reference. Alternatively, an antibody antigen pair is utilized to bind a polymerase enzyme to a support surface whereby the support surface is coated with an antibody that recognizes an epitope on the protein antigen. When the antigen is introduced into the reaction chamber it is reversibly bound to the antibody and immobilized on the support surface. A lack of interference with catalytic activity in such a method has been reported for HIV reverse transcriptase. Lennerstrand, *Analytical Biochemistry*, 1996; 235: 141-152, which is hereby incorporated by reference. Additionally, DNA polymerase immobilization has been reported as a functional immobilization method in Korlach et al., U.S. Pat. No. 7,033,764 B2; incorporated herein by reference. Finally, any protein component can be biotinylated such that a biotin streptavidin interaction is optionally created between the support surface and the target immobilized antigen.

Preferably, the target DNA strand and replication machinery remain free in solution. It is appreciated that the solution is suitable to permit diffusion, incorporation, synthesis of a second complementary strand in each of the reaction chambers. In a non-limiting example suitable solution contains 50 mM Tris-HCl pH 8.0, 25 nM magnesium chloride, 65 mM sodium chloride, and 3 mM DTT. It is appreciated that other solution components and types are similarly operable and optimized for the particular polymerase or template being utilized.

The inventive process is optionally initiated in a solution containing one or more DNA template strands and the appropriate number of monomers of each species. In each chamber a reaction is optionally initiated by the addition of a nucleic acid polymerizing enzyme. In an alternative embodiment a primed target DNA strand sequence is established by pre-addition of a target sequence, a primer, and the appropriate number of monomers or each species. No synthesis of a complementary second strand occurs in the absence of a DNA polymerase. The reaction is optionally initiated by addition of the replication machinery. In an alternative embodiment all components of the replication machinery are present including the DNA polymerase, the template molecule, the primer, and monomers. The solution in this embodiment is optionally void of necessary ions for the function of the polymerase enzyme. For example, the reaction is optionally initiated by the addition of magnesium ions such that the replication machinery now becomes functional. In yet another alternative embodiment all of the reaction machinery is present, however, the reaction chamber is heated above a threshold temperature above the melting temperature of the template molecule and the primer such that hybridization between the primer and the template molecule does not occur. The polymerization reaction begins by adjusting the temperature to a suitable reaction temperature.

Each reaction chamber is optionally in fluidic connection with a detector such that by washing each of the chambers free monomers are transported to the detector area and are readily detected. In a preferred embodiment each of the monomer species is differentially labeled such that it can be easily distinguished from other species.

In an alternative embodiment a sampling of each of the reaction chambers is obtained and injected into a mass spectrometer to recognize and quantitate the presence of free monomers. This embodiment has the advantage of using native, non-labeled monomers whereby greater efficiency and accuracy of the polymerase is achieved. Alternatively, it is appreciated that multiple detector types are optionally employed. In a non-limiting example, monomers are fluorescently labeled. Detection of free monomers is, thus, detected by a fluorometer.

In a preferred embodiment the template strand is bound to a support. An optional fluidic connection between each reaction chamber and the detector is such that the large template molecule remains in the chamber while the small monomers are readily transported through a barrier such as a size exclusion membrane or an electrophoretic gel. As such, a sampling of each reaction chamber is optionally achieved for detection of the presence of free monomers.

It is appreciated that the sequence of the template DNA strand is independent of the inventive process and that the inventive process is operable on any known or unknown sequence of monomers in a template strand. Preferably, the target sequence is a DNA sequence that corresponds to a known sequence. Preferably, the known sequence is a gene. Most preferably, a gene is a previously discovered and sequenced DNA strand such that the wild-type sequence is known. Knowledge of a wild-type sequence is not required prior employing the inventive process. Methods of DNA sequencing are known in the art and any unknown sequence is readily identifiable without undue experimentation by a person having ordinary skill in the relevant art. Any method of DNA sequencing known in the art is operable herein.

It is appreciated that numerous other embodiments of the instant invention exist with greater or fewer reaction chamber numbers, types, sizes, interconnections, or pathways and are also the subject of the instant invention.

Various aspects of the present invention are illustrated by the following non-limiting examples. The examples are for illustrative purposes and are not a limitation on any practice of the present invention.

Example 1

A standard reaction chamber protocol is outlined in FIG. 1. A 30-mer DNA template strand with a known sequence of 3'-ATG CAT GCA TGC ATG CAT GCA TGC ATG CAT 5' (SEQ ID NO: 1) is amplified by standard PCR techniques and purified on an anion exchange resin supplied by Quiagen, Inc., Valencia, Calif. $1 \times 10^{10}$ copies of template is added to each of four reaction chambers each containing a reaction solution of 60 mM Tris-$SO_4$ (pH 8.9), 180 mM Ammonium Sulfate. A primer (8 μg) of complementary sequence 5'-TAC GTA CGT ACG TAC GTA CGT ACG TAC GTA-3' (SEQ ID NO: 2) is added to each chamber and allowed to hybridize with the DNA template under suitable conditions. Monomers: A, T, G, and C nucleotides obtained from Perkin Elmer, Waltham, Mass. are added to each of the four reaction chambers. As the template extends 16 nucleotides beyond the primer, 16 monomers of the specific species are added to each respective reaction chamber for each template strand. As the known template strand in the instant example is a ATCG repeat sequence, each base will be added to a reaction chamber at $1.6 \times 10^{11}/4$ copies per chamber. Additionally, 1 number percent ($1.6 \times 10^{9}/4$) copies excess of each monomer species is added to each reaction chamber. A polymerization reaction is initiated by the addition of 1 unit (final) of Platinum® Taq DNA Polymerase (Invitrogen, Inc., Carlsbad, Calif.) along with 2 mM $MgSO_4$ (final) in reaction solution. The reaction is allowed to proceed for 2 min. A sample of free nucleotide is selectively moved from the reaction chamber and detected by liquid chromatography mass spectrometery on an API 4000 tandem quadrapole mass spectrometer (Applied Biosystems, Foster City, Calif.).

FIG. 1A depicts hybridization of a complementary second DNA strand with T $1.6 \times 10^{11} + 1.6 \times 10^{9}$ excess T mononucleotides hybridizing to a polyA strand in the target sequence such that full synthesis of a complementary strand is achieved leaving $1.6 \times 10^{9}$ copies of T will remain in the chamber following polymerization. FIG. 1B the template strand possesses a single A to G mutation. Thus, the T present in the reaction chamber does not hybridize with the G and the polymerization reaction stalls. Thus, detection by mass spectrometery will identify a large excess of T indicating the presence of the mutation. FIG. 1C1-C4 represent the subsequent addition of $1 \times 10^{10}$ copies of a each of a single species of monomer is added to each of four chambers. Only the chamber wherein the monomer C was added does polymerization occur and the number of monomers is depleted by the incorporation. Thus, the chambers represented in FIGS. 1C2-1C4 will have $1 \times 10^{10}$ excess monomers than chamber depicted in 1C1. Thus, the identity of the mutation is established. The location of the mutation is obtainable by full sequencing techniques known in the art.

Example 2

Identification of coagulation factor IX mutations leading to hemophilia B: The human coagulation factor IX gene maps to chromosome Xq27 spanning spans about 34 kilobases of genomic DNA. Roberts HR. *Thromb Haemost*, 1993; 70:1-9. The entire gene, including introns, was cloned in 1982 and sequenced in 1985. Choo K H, Gould K G, Rees D J, Brownlee, G G., *Nature*, 1982; 299:178-80; Yoshitake S, Schach B G, Foster D C, Davie, E W, Kurachi K., *Biochemistry*, 1985; 24:3736-50.

Genomic DNA is obtained from human subject A with a mild bleeding phenotype, and human subject B with no known bleeding phenotype as described by Hinks J L, Winship P R, Makris M, Preston, F E, Peake I R, Goodeve A C, *Br J Haematol*, 1999; 104: 915-8 the entire contents of which are herein incorporated by reference. Primers for sequencing the factor IX gene along with annealing temperature for amplification and synthesis of complementary strands and $MgCl_2$ concentrations are as used by Belvini, D, et al, *Haematologica*, 2005; 90:635-642 which is incorporated herein by reference, with particularity the methods and Table 1.

Each family of primers is used to amplify a particular region of DNA until a suitable number of copies are available. The DNA is purified and separated into single strand fragments and quantified by methods known in the art. For each amplified segment of genomic DNA amplified from each of subjects A and B, 1000 copies of each gene section are placed in a family of four reaction chambers housing a buffer solution containing 75 mM Tris-HCl, pH 8.8, 20 mM $(NH_4)_2SO_4$, 0.001% Tween-20) in a final volume of 50 μl. Reaction chambers are a 96-well PCR amplification plate to facilitate the large number of wells required including triplicate repeats. The use of a plate also facilitates rapid detection of mutation in a large number of positions in a long gene sequence such as factor IX. The nucleotide content of each gene segment is calculated based on the known wild-type sequence. A stoichiometric amount of each nucleotide based on the known wild-type sequence is added to each chamber along with 100 ng of the complementary primer. A one number percent of excess number of copies of each nucleotide monomer is added to each chamber followed by addition of 1.25 U Taq DNA polymerase, and the amplification reaction is allowed to proceed to completion (~2 min).

A sample of free nucleotide is selectively moved from the reaction chamber and detected by liquid chromatography mass spectrometry on an API 4000 tandem quadrupole mass spectrometer (Applied Biosystems, Foster City, Calif.). Each of the chambers from subject A held an excess of monomers suggesting the presence of a mutation in the corresponding region originally amplified. However, subject B demonstrated no excess nucleotide monomers in any chamber indicating that no mutation is present. To determine the type of mutation in subject A, 1000 copies of a single nucleotide monomer species is added to each of the four reaction chambers indicating a mutation. Polymerization is allowed to proceed to completion (~2 min) and a sample of each chamber is analyzed by LC/MS/MS. The tube with G. monomer added demonstrated a decrease in the number of free nucleotides present in solution as determined by mass spectrometry suggesting a mutation to a C nucleotide in the subject's gene.

The segment demonstrating a wild-type to C mutation in patient A is subjected to sequencing as described by Belvini, 2005. Sequence analysis demonstrates that subject A has a T→4C missense mutation at position 111. This mutation corresponds to mild hemophilia B.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

We claim:

1. A process of identifying the existence of a mutation in a DNA strand without DNA sequencing comprising:
   placing a plurality of DNA single strands of a DNA sequence in a solution with a stoichiometric quantity of monomeric nucleotide bases to synthesize complementary second strands to said plurality of DNA single strands in the presence of reagents and buffers comprising nucleic acid polymerizing enzymes and accessory proteins or molecules and conditions for DNA synthesis:
   adding a small excess of said monomeric nucleotides bases beyond the said stoichiometric quantity of monomeric nucleotide bases;
   allowing sufficient time for DNA synthesis; and
   determining a quantity of monomeric nucleotide bases remaining in the solution after DNA synthesis is more than the said small excess of said monomeric nucleotides bases as being indicative of a mutation being present in said plurality of DNA single strands.

2. The process of claim 1 wherein said plurality of DNA single strands of a DNA sequence is a known DNA sequence.

3. The process of claim 1 wherein said plurality of DNA single strands of a DNA sequence is a DNA sequence with a mutation.

4. The process of claim 3 wherein said mutation is one or more single nucleotide polymorphisms.

5. The process of claim 1 wherein said plurality of DNA single strands is in excess of 500 copies and said small excess of monomeric nucleotides bases is between 0.3 and 3 number percent of said stoichiometric quantity of monomeric nucleotide bases.

6. The process of claim 5 wherein said small excess of monomeric nucleotides bases is between 0.5 and 1.5 number percent of said stoichiometric quantity of monomeric nucleotide bases.

7. The process of claim 1 further comprising:
adding a single type monomer possibly depleted in the solution after DNA synthesis under conditions for DNA synthesis; and
detecting the presence or absence of synthesis of the complementary second strand.

8. The process of claim 7 further comprising repeating the adding and detecting steps with other single monomer species other than the single type monomer species in the solution or an aliquot of the solution.

9. The process of claim 7 wherein four separate monomers of A, T, C and G are added to aliquots of the solution.

10. The process of claim 7 further comprising sequencing the DNA single strand before or after synthesis of said complementary second strands.

* * * * *